United States Patent
Fernandes et al.

(10) Patent No.: US 6,401,523 B1
(45) Date of Patent: Jun. 11, 2002

(54) DEVICE FOR TESTING ROCK SAMPLES AT RELATIVELY HIGH PRESSURE AND TEMPERATURE

(75) Inventors: Gérard Fernandes, Nanterre; José Brandely, Savigny sur Orge; Dominique Garnier, Orgeval, all of (FR)

(73) Assignee: Institut Francais du Petrole, Rueil-Malmaison cedex (FR)

( * ) Notice: Subject to any disclaimer, the term of this patent is extended or adjusted under 35 U.S.C. 154(b) by 0 days.

(21) Appl. No.: 09/435,785

(22) Filed: Nov. 8, 1999

(51) Int. Cl.$^7$ .......................... G01N 15/08; G01N 3/00; G01N 15/10; H05G 1/00
(52) U.S. Cl. ........................... 73/38; 73/37; 73/152.07
(58) Field of Search .......................... 73/37, 38, 152.07

(56) References Cited

U.S. PATENT DOCUMENTS

| | | | |
|---|---|---|---|
| 4,688,238 A | * 8/1987 | Sprunt et al. ............ | 378/4 |
| 4,710,948 A | * 12/1987 | Withjack ............ | 378/208 |
| 4,753,107 A | * 6/1988 | Reed et al. ............ | 73/38 |
| 4,827,761 A | * 5/1989 | Vinegar et al. ............ | 73/38 |
| 5,065,421 A | * 11/1991 | Morineau et al. ............ | 378/208 |
| 5,167,139 A | * 12/1992 | Lafargue et al. ............ | 73/38 |
| 5,265,461 A | * 11/1993 | Steiger et al. ............ | 73/38 |
| 5,325,723 A | * 7/1994 | Meadows et al. ............ | 73/794 |
| 5,591,902 A | 1/1997 | Castagner ............ | 73/84 |
| 5,679,885 A | * 10/1997 | Lenormand et al. ............ | 73/38 |
| 5,698,772 A | 12/1997 | Deruyter et al. ............ | 73/38 |
| 5,731,511 A | * 3/1998 | Roque et al. ............ | 73/38 |
| 5,811,308 A | 9/1998 | Espitalie et al. ............ | 436/145 |
| 5,979,223 A | * 11/1999 | Fleury ............ | 73/38 |

* cited by examiner

*Primary Examiner*—Hezron Williams
*Assistant Examiner*—David J. Wiggins
(74) *Attorney, Agent, or Firm*—Antonelli, Terry, Stout & Kraus, LLP

(57) ABSTRACT

Device for studying physical properties of a solid sample (S) in the presence of fluids, at relatively high temperature and pressure. The device comprises an elongate rigid body (1) closed at the opposite ends thereof by two covers (2, 3), a flexible sheath (9) around the sample, cooperating with two end pieces (7, 8) so as to delimit, inside the rigid body, a containment vessel, injection means for displacing fluids under pressure through the sample in its sheath, measuring means for measuring various parameters of the sample and means (P) for injecting a fluid under pressure around flexible sheath (9) so as to exert a radial pressure and possibly an axial pressure around the sample, means for heating the fluid under pressure associated with at least one of the two covers (3, 4) and means including a turbine (12) for example, for homogenizing the temperature around the sheath by circulation of the fluid heated on contact with the heating means. The body is preferably made of a composite material. The device can be applied for: study of geologic samples for example.

14 Claims, 2 Drawing Sheets

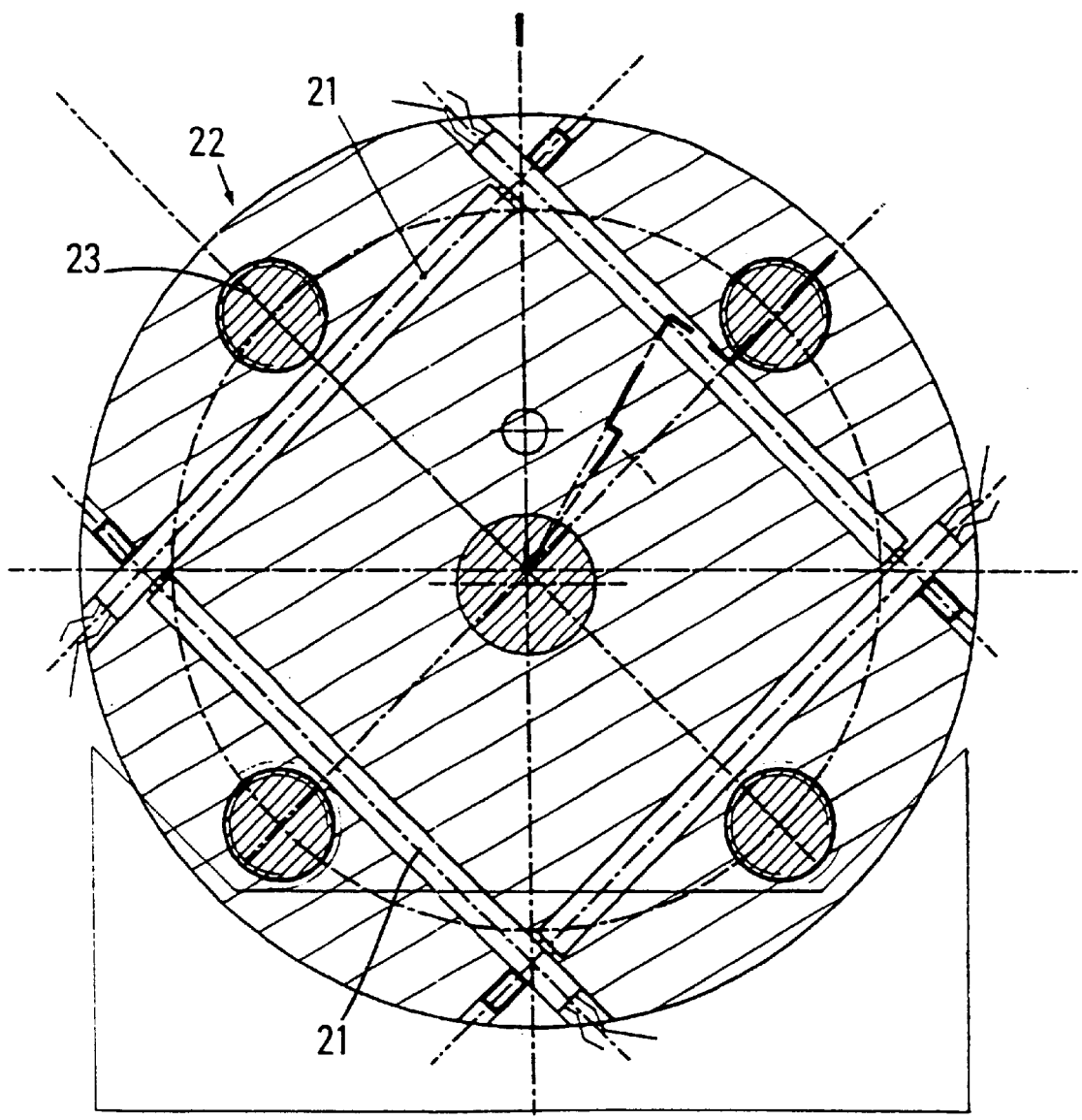

DEVICE FOR TESTING ROCK SAMPLES AT RELATIVELY HIGH PRESSURE AND TEMPERATURE

FIELD OF THE INVENTION

The present invention relates to a device for studying physical properties of solid samples in the presence of fluids, at high temperature and pressure.

The device according to the invention is suited for testing for example geologic samples and for determining various parameters such as the capillary pressure of rocks in drainage or imbibition phases, their wettability index, their relative permeability, their resistivity index, etc, under temperature and pressure conditions reproducing those found in reservoirs containing or likely to contain hydrocarbons and from which they are taken.

BACKGROUND OF THE INVENTION

In order to determine the distribution of the oil and gas volumes in a reservoir, the values of the saturations that depend on parameters such as the wettability and the interfacial tension have to be known at any point. The wettability of rocks with regard to the water and to the oil that may be contained therein is therefore determined. The rock must therefore be subjected to drainage operations, i.e. displacement of the fluids in order to decrease the water saturation, followed by imbibition operations, this term referring to displacement of the fluids allowing to increase the water saturation (Sw) of the rock. The capillary pressure at one point of a porous material containing two fluids such as water and oil in the continuous phase is defined, as it is well-known, as the difference Pc at equilibrium between the pressure P(oil) of the oil and the pressure P(water) of the water.

Knowledge of various parameters and notably of the wettability of the rocks is useful notably when enhanced recovery is to be performed in a formation, by draining the effluents contained therein by injection of a fluid under pressure, and when the most suitable fluid (water or gas) for effluent displacement is to be selected by means of preliminary tests.

Various types of devices are used to carry out these drainage and imbibition operations in the laboratory. The sample bars are generally placed in a cell. At the opposite ends thereof, the cell comprises two end pieces communicating with means intended to establish displacement of fluids under pressure through the sample tested. Measuring means are used to measure various parameters pressures, saturations, electric resistivity, etc. The sample bar can be placed inside an elastomer containment vessel compressed by injection of fluid under pressure.

Various devices for measuring physical parameters of porous solid samples are described for example in patents FR-2,708,742, FR-2,724,460 (U.S. Pat. No. 5,610,525) or FR-2,728,684 (U.S. Pat. No. 5,637,796) filed by the applicant.

Monitoring of the displacement of the fluids in a sample is often performed by using X-ray or gamma-ray investigation means exterior to the cell. The walls of the cell body must be sufficiently resistant to withstand confining pressures of several ten MPa while remaining transparent to the radiation and therefore relatively thin.

Conventional means for maintaining the sample at a relatively high temperature (150° C. for example) : drying oven or heating jackets wound around the body, are hardly compatible with the use of a radiation investigation device because they are interposed between the latter and the sample, and they contribute still further to radiation attenuation.

SUMMARY OF THE INVENTION

The device according to the invention allows to measure physical properties of a sample at relatively high pressure and temperature, while avoiding notably the drawbacks of the prior art.

The device comprises an elongate rigid body closed at the opposite ends thereof by two end pieces, a flexible sheath around the sample, cooperating with the two end pieces so as to delimit a containment vessel inside the rigid body, means for establishing displacement of fluids under pressure through the sample in its vessel, means for measuring various parameters of the sample and means for injecting a fluid under pressure around the flexible sheath so as to exert a radial pressure around the sample.

The device comprises means for heating the fluid under pressure (such as electric resistors) associated with at least one of the two covers and means for homogenizing the temperature around the sheath by circulation of the fluid heated on contact with the heating means.

The fluid circulation means comprise for example a stirring means cooperating with a circuit intended to circulate the fluid in contact with the heating means.

According to an embodiment, the stirring means comprises a turbine driven by a motor, that is placed in a cavity of one of the two covers, and the circuit intended for circulation of the fluid in contact with the heating means comprises a tube placed in the annular space between the body and the sheath, this tube communicating lines interior to the two covers.

According to a preferred embodiment, the body comprises a tubular part made of a composite material, the two covers being made of a good heat-conducting material.

The covers can be secured to the body either directly or by means of ties that can also be made of a composite material.

The device comprises for example channels provided through the two covers for communicating the ends of the sample with fluid circulation means.

The measuring means can comprise a device for measuring the absorption of a radiation by said sample.

The heating mode used is advantageous because it is simple and effective. The heating means are in direct contact with the sample, which allows to reduce the time required for uniform temperature distribution. Furthermore, no exterior element likely to absorb radiations emitted by measuring devices exterior to the body is interposed, the radiation measuring sensitivity being thus improved.

Using a body made of a composite material also allows to limit the required thickness compatible with the high pressures necessary for measuring operations. The low absorption of radiations emitted by the measuring devices exhibited by such a material furthermore allows to facilitate the implementation thereof.

BRIEF DESCRIPTION OF THE DRAWINGS

Other features and advantages of the device according to the invention will be clear from reading the description hereafter of a non-limitative realisation example, with reference to the accompanying drawings wherein:

FIG. 2 is a cross-sectional view of an end cover with built-in heating means.

DETAILED DESCRIPTION OF THE INVENTION

Figure 1:
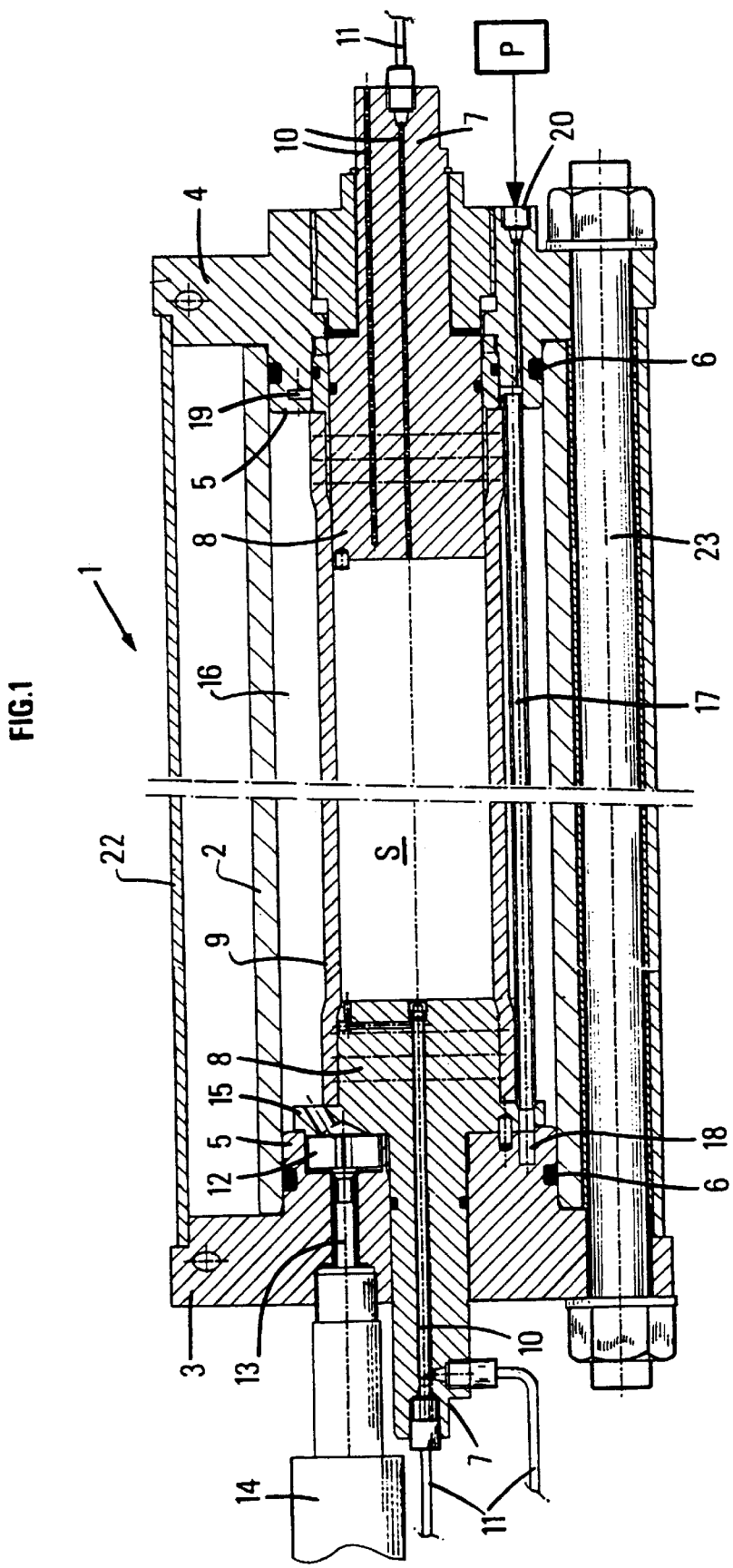
FIG. 1 is a lengthwise cross-sectional view of the cell.

The device comprises a hollow body 1 consisting of a tubular part 2 closed at the two opposite ends thereof by two covers 3, 4 provided each with a shoulder 5 equipped with seals 6, fitting closely into tubular part 2. The device comprises two end pieces made from a good heat-conducting material, consisting each of a rod 7 and of a head 8 of larger section than the section of the rod but smaller than that of tubular part 2. Each cover 3, 4 comprises an axial bore for a rod 7. The sample S to be tested is placed in a flexible sheath 9 made of elastomer for example, whose opposite ends are fitted onto heads 8. Channels 10 and connection means for outer lines 11 connected to pumping means (not shown), allowing displacement of fluids inside sample S as described in the aforementioned prior patents, run right through each end piece.

A cavity is provided in cover 3 for a turbine 12. A bore 13 parallel to the axis of body 1 is provided through cover 3, allowing connection of the turbine shaft with a driving motor 14. The cavity of the turbine communicates through a channel 15 with the annular space 16 between sheath 9 and tubular part 2. A fine tube 17 is placed in annular space 16 between the heads 8 of the two end pieces. It communicates at a first end with the cavity of turbine 12 by means of a circular groove 18 in cover 3, and at the opposite end thereof with annular space 16 by means of a second circular groove 19 in second cover 4. A channel 20 provided through second cover 4 allows to communicate annular space 16 with means P for injecting a fluid under pressure (oil for example) intended to exert a radial pressure on sample S by means of flexible sheath 9. Passages (FIG.2) are provided in each cover 3, 4 for electric resistors 21 connected to a power supply (not shown).

The two end covers 3, 4 fit into a cylinder 22 forming a brace and are tightly fastened against tubular part 2 by several ties 23.

The device is operated as follows:

Sample S being positioned between the two heads of the end pieces and the covers being adjusted and fastened to the body, a fluid under pressure is injected into annular space 16 through channel 20. Electric resistors 21 intended to heat the two covers 3, 4 are then supplied and turbine 12 is actuated. The fluid circulates from one end of annular space to the other through tubes 17 and end transfer channels 15, 18, 19. It is permanently heated as it passes inside covers 3, 4 that are brought to a high temperature by electric resistors 21. Thanks to this stirring and permanent heating, the oil in annular space 16 and therefore sample S can be quickly brought to a homogeneous temperature reproducing for example the temperature that prevails in the subsoil at the depth where it has been taken.

A radiation sample analysis device can be placed on the periphery of cylinder 22 in the angular sectors between ties 23. Tubular part 2 and cylinder 22 are preferably made of a composite material. Its intrinsic rigidity thus advantageously allows to decrease their thickness and simultaneously their capacity to absorb the radiations emitted by the radiation investigation equipments that can be arranged around the device. The heat conductivity is also lower than that of the metals used (aluminium for example), which has the beneficial effect of decreasing the radiation heat losses and therefore of reaching the temperature required for the purpose of the tests more rapidly.

Ties 23 can also be made of a composite material so as to no longer hinder penetration of the radiation emitted by the measuring devices and thus to allow the making of measurements over the total periphery of the rigid body.

A layout where ties 23 are used to secure the covers to the peripheral part 2 of body 1 has been described. Direct fastening of the covers to the body may however be preferred, which allows to totally clear the periphery of the body, to obtain a more compact device and to simplify installation of sample investigation devices around and along sample S.

We claim:

1. A device for studying physical properties of a solid sample in the presence of fluids, at relatively high temperature and pressure, comprising an elongate rigid body closed at the opposite ends thereof by two covers, a flexible sheath within which the sample is to be provided, cooperating with two end pieces so as to delimit, inside the rigid body, a containment vessel, means for establishing displacement of fluids under pressure through the sample in its sheath, measuring means for measuring various parameters of the sample and means for injecting a fluid under pressure into an annular space around the flexible sheath so as to exert a radial pressure around the sample, the device also comprising means for heating the fluid under pressure associated with at least one of the covers and circulation means for circulating around the sheath the fluid under pressure heated on contact with the heating means and for homogenizing the temperature of the sample.

2. A device as claimed in claim 1, wherein the heating means comprises electric resistors associated with at least one of said covers.

3. A device as claimed in claim 2, wherein the fluid circulation means comprise a stirring means cooperating with a circuit intended for circulation of the fluid in contact with the heating means.

4. A device as claimed in claim 2, wherein the body comprises a tubular part made of a composite material, the two covers being made of a good heat-conducting material.

5. A device as claimed in claim 3, wherein the stirring means includes a turbine driven by a motor, placed in a cavity of one of said covers, and the circuit intended for circulation of the fluid in contact with the heating means comprises a tube placed in the annular space between the elongate rigid body and the flexible sheath, said tube communicating with lines interior to the covers.

6. A device as claimed in claim 4, also including means for direct fastening of the two covers to tubular part of the body.

7. A device as claimed in claim 1, wherein the fluid circulation means comprise a stirring means cooperating with a circuit intended for circulation of the fluid in contact with the heating means.

8. A device as claimed in claim 7, wherein the stirring means includes a turbine driven by a motor, placed in a cavity of one of said covers, and the circuit intended for circulation of the fluid in contact with the heating means comprises a tube placed in the annular space between the elongate rigid body and the flexible sheath, said tube communicating with lines interior to the covers.

9. A device as claimed in claim 1, wherein the body comprises a tubular part made of a composite material, the two covers being made of a good heat-conducting material.

10. A device as claimed in claim 9, also including means for direct fastening of the two covers to the tubular part of the body.

11. A device as claimed in claim 1, wherein the covers are fastened to the elongate rigid body by ties.

12. A device as claimed in claim 11, wherein the ties are made of a composite material.

13. A device as claimed in claim 1, also including channels provided through the two covers for communicating opposite ends of the sample with fluid circulation means.

14. A device as claimed in claim 1, wherein the measuring means includes an instrument for measuring absorption of a radiation by said sample.

\* \* \* \* \*